(12) United States Patent
Stokes et al.

(10) Patent No.: US 7,758,816 B2
(45) Date of Patent: Jul. 20, 2010

(54) LARGE AREA CYTOCENTRIFUGE SAMPLE CHAMBER

(75) Inventors: Barry O. Stokes, Logan, UT (US);
Kevin M. Mullen, Smithfield, UT (US);
Patti A. Nelson, Paradise, UT (US);
Randal P. Holman, Logan, UT (US)

(73) Assignee: Wescor Inc., Logan, UT (US)

( * ) Notice: Subject to any disclaimer, the term of this patent is extended or adjusted under 35 U.S.C. 154(b) by 507 days.

(21) Appl. No.: 11/713,470

(22) Filed: Mar. 1, 2007

(65) Prior Publication Data
US 2008/0214378 A1   Sep. 4, 2008

(51) Int. Cl.
*G01N 1/28* (2006.01)

(52) U.S. Cl. .................. 422/102; 422/72; 422/100; 422/101; 422/104; 436/177; 436/178; 436/180; 73/863.22; 494/37; 137/544; 137/546

(58) Field of Classification Search ............ 422/72, 422/100, 101, 102, 104; 436/177, 178, 180; 73/863.22; 494/37; 137/544, 546
See application file for complete search history.

(56) References Cited

U.S. PATENT DOCUMENTS

| | | | |
|---|---|---|---|
| 4,192,250 A * | 3/1980 | van Duijn | 118/52 |
| 4,250,830 A * | 2/1981 | Leif | 118/52 |
| 4,306,514 A | 12/1981 | Bouclier | |
| 4,314,523 A | 2/1982 | Boeckel et al. | |
| 4,327,661 A | 5/1982 | Boeckel | |
| 4,391,710 A | 7/1983 | Gordon | |
| 4,423,699 A | 1/1984 | Boeckel et al. | |
| 4,428,323 A | 1/1984 | Wells | |
| 4,574,729 A | 3/1986 | Wells | |
| 4,576,110 A | 3/1986 | Wells | |
| 4,612,873 A * | 9/1986 | Eberle | 118/52 |
| 4,678,579 A | 7/1987 | Griffin | |
| 4,696,743 A * | 9/1987 | Gordon et al. | 210/361 |
| 4,853,188 A * | 8/1989 | Toya | 427/2.11 |
| 4,874,582 A | 10/1989 | Gordon et al. | |

(Continued)

FOREIGN PATENT DOCUMENTS

GB   2089063   6/1982

(Continued)

*Primary Examiner*—Jill Warden
*Assistant Examiner*—Shogo Sasaki
(74) *Attorney, Agent, or Firm*—Thorpe North & Western LLP (57) ABSTRACT

A cytocentrifuge sample chamber includes a sample receiving well to receive and hold a sample to be centrifuged and a sedimentation chamber adjacent a microscope slide upon which cells and/or other sediment material in the sample is to be deposited. A passage, such as a spillway, connects the sample receiving well and the sedimentation chamber, so that sample flows from the sample well under the influence of centrifugal force as centifugation begins into the sedimentation chamber where the sample is forced by centrifugal force against the microscope slide leaving a vacant space at the inner end of the sedimentation chamber. Sedimentation of the sample takes place against the microscope slide. When centrifugation ends, the liquid components of the sample flow back into the vacant space in the sedimentation chamber and can be removed from the vacant space at the inner end of the sedimentation chamber through a removal chamber. This avoids contamination of equipment and users and allows a secondary centrifugation to take place.

36 Claims, 9 Drawing Sheets

U.S. PATENT DOCUMENTS

| | | | |
|---|---|---|---|
| 5,180,606 A * | 1/1993 | Stokes et al. | 427/2.13 |
| 5,252,228 A | 10/1993 | Stokes et al. | |
| 5,380,435 A | 1/1995 | Stokes et al. | |
| 5,466,371 A | 11/1995 | Barlow et al. | |
| 5,470,758 A | 11/1995 | Hayes | |
| 5,480,484 A * | 1/1996 | Kelley et al. | 118/52 |
| 5,589,400 A | 12/1996 | Hayes | |
| 5,679,154 A * | 10/1997 | Kelley et al. | 118/52 |
| 5,942,129 A | 8/1999 | Hayes | |
| 5,952,239 A * | 9/1999 | Hayes et al. | 436/177 |
| 6,162,401 A * | 12/2000 | Callaghan | 422/104 |
| 6,436,662 B1 | 8/2002 | Mielzynska et al. | |
| 6,890,729 B2 | 5/2005 | Mielzynska et al. | |
| 2004/0007650 A1 | 1/2004 | Cortelazzo | |
| 2005/0260100 A1* | 11/2005 | Leif | 422/72 |
| 2006/0135337 A1* | 6/2006 | Kerrod et al. | 494/15 |

FOREIGN PATENT DOCUMENTS

| | | |
|---|---|---|
| JP | 57211066 A * | 12/1982 |
| WO | WO 2005019806 A1 * | 3/2005 |

\* cited by examiner

FIG. 15b

LARGE AREA CYTOCENTRIFUGE SAMPLE CHAMBER

BACKGROUND OF THE INVENTION

1. Field

The invention is in the field of cytocentrifugation devices used to centrifugally deposit sediment material, such as cells, from a sediment containing sample onto a microscope slide, and particularly in the field of sample chambers for receiving the sample and applying the sample to the microscope slide in such devices.

2. State of the Art

Cytocentrifugation devices are small centrifuges particularly designed for centrifuging small samples of body fluids, such as blood, to separate cells or other sediment materials therefrom and deposit the cells or other sediment materials onto a microscope slide for further examination and evaluation. Cytocentrifugation devices generally include a rotor to which a plurality of sample receiving chambers in association with microscope slides are removably secured. The fluid sample containing the sediment material to be examined is placed into a sample receiving well in the sample chamber. During centrifugation, the sample flows by centrifugal force against the microscope slide so that cells or other sediment materials in the sample are forced against the microscope slide and generally adhere thereto. During centrifugation, the sample is held in a sedimentation chamber against the microscope slide which forms an end of the sedimentation chamber. The sedimentation chamber may serve as the sample receiving well, or the sample receiving well may be separated from the sedimentation chamber and arranged so that the sample flows from the sample receiving well into the sedimentation chamber upon the start of centrifugation. After the centrifugation, the sample receiving chamber is removed from the cytocentrifugation device and the microscope slide is also removed from the cytocentrifugation device for examination and evaluation. Depending upon the cytocentrifugation device, the sample chamber and microscope slide may be removed from the cytocentrifugation device as a unit with the microscope slide later separated from the sample chamber for examination and evaluation, or the two can be removed from the cytocentrifugation device separately. However, in either case, it is desirable that the liquid portion of the sample be removed from contact with the microscope slide at the termination of centrifugation so that the liquid does not interfere with the sediment deposited on the slide and so that the slide and sample chamber can be removed from the cytocentrifuge device or otherwise separated from one another without the mess and possible contamination that might result from the liquid running uncontrollably out of the sedimentation chamber.

Several methods have been used to remove the liquid portion of the sample from around the microscope slide either during centrifugation or when centrifugation stops. In some sample chambers, a removal passage is provided leading from the opening of the sedimentation chamber against the microscope slide to a collection system. A vacuum source is connected to the removal passage to suck the sample liquid from the sedimentation chamber after centrifugation stops. Examples of such sample chambers are shown in U.S. Pat. Nos. 4,306,514, 4,314,523, 4,327,661, 4,423,699, and 4,428,323. These systems all require the complication of providing vacuum lines connected to arms of the centrifuge rotor, and the use of a vacuum waste collection system.

Systems having liquid removal passages have been developed where absorbent material is positioned in the removal passage to eliminate the need for the vacuum source. The sample liquid is drawn from the sedimentation chamber-microscope slide interface by the absorbent material in the removal passage. Examples of these systems are shown in U.S. Pat. Nos. 4,574,729 and 4,576,110. A problem with systems using absorbent material in a removal passage to absorb the liquid portion of the sample is that the absorption of the sample by the absorbent material begins before the centrifugation of the sample is completed. This means that a portion of the sample with sediment material is lost in the removal passage before such sediment can be deposited on the slide. This reduces the number of cells or the amount of other sediment material that can be deposited on the slide reducing the effectiveness of the separation of the sediment materials from the liquid portion of the sample.

Many cytocentrifuge systems currently in use position absorbent material, such as filter paper or filter card, between the end of the sedimentation chamber and the microscope slide around the periphery of the sedimentation chamber opening to allow and control flow of sample liquid into the filter paper or card so that the sample liquid is slowly but completely absorbed by the filter paper or filter card by the end of centrifugation. Examples of these systems are shown in U.S. Pat. Nos. 4,391,710, 4,678,579, 5,252,228, 5,380,435, and 5,466,371. These systems are designed to be used with small samples of material to be evaluated. Thus, such systems normally have sample chambers to hold about 300 to 500 microliter samples, with some holding up to about one milliliter of sample. In some situations, it is desirable to use larger samples, up to about twelve milliliters, and usually up to about six milliliters. This is the case where it is desirable to have more cells from a sample for observation than are available in a small sample of less than about 1 milliliter. However, with large volume samples, it is impractical to absorb all of the sample liquid at the sample chamber-microscope slide interface under centrifugal force. With large volume samples, it is necessary to provide a seal between the sample chamber and the microscope slide so that sample fluid does not escape during centrifugation and to provide for removal of the sample liquid after centrifugation is completed. While the vacuum removal system referred to earlier can be used in such circumstances, a simpler system is preferred.

An approach to removal of the sample liquid from the sedimentation chamber-microscope slide interface when centrifugation is completed is to make the sedimentation chamber slope downwardly away from the microscope slide so that the sample is held in the lower portion of the sedimentation chamber when centrifugation is not taking place. However, the sloping of the chamber downwardly so that the top and bottom sedimentation chamber walls are not aligned with the centrifugal force applied to the sample, has been found to result in uneven distribution of the sediment on the microscope slide giving a concentration of cells at the bottom of the sample area and weak cell densities at the top of the sample area. A further problem in using larger sample volumes and larger sample chambers is that the cells or other sediment materials tend to settle in the sample chamber prior to centrifugation and are applied unevenly to the microscope slide during centrifugation. U.S. Pat. Nos. 5,470,758 and 5,589,400 address this problem by providing a sample chamber for a large sample, wherein the sample receiving well, which also serves as the sedimentation chamber to hold the sample during centrifugation and application to the microscope slide, is not only sloped downwardly, but is also provided with a plurality of baffle plates therein which define a tortuous path for sample flowing into the sample receiving well as the sample receiving well is filled. The baffle plates collect some of the sediment in the sample fluid on the baffle plates as the sample fills the sample receiving well and sedimentation chamber prior to centrifugation. The baffle plates spread the sediment throughout the chamber rather than allowing it all to settle in the bottom of the chamber.

As indicated, in the device of U.S. Pat. Nos. 5,470,758 and 5,589,400, the sedimentation chamber is slopped downwardly so that the sample placed in the sedimentation chamber remains in the lower part of the chamber away from the microscope slide until centrifugation takes place. At that time, the sample chamber rotates slightly, but the chamber still remains at a sloped orientation to the microscope slide. The sample is forced to the upper end of the sedimentation chamber and against the microscope slide by the centrifugal force of the centrifugation. At the end of centrifugation, the sample liquid decants and flows by gravity back into the lower portion of the sedimentation chamber and away from the slide. The use of the baffles in the sedimentation chamber to spread the sediment material has not solved the problem of uneven distribution of the sample on the slide. It has been found in use of such baffled chamber that rather than an even disposition of sediment on the slide, the sediment is applied to the microscope slide in striations corresponding to the baffle locations. This is in addition to the weaker cell densities at the top of the sample area due to the sloping chamber. In addition, with the sample retained in the lower portion of the sedimentation chamber, avoiding spillage of the decanted fluid during chamber removal requires some care in handling. Further, the fluid does not always decant completely and droplets can remain on the microscope slide where the chamber contacts the slide surface primarily at the bottom of the collection area. When the chamber is pulled away from the slide, these droplets can flow down on the slide and contaminate the rotor. Also, the residual fluid can cause smearing of the sample and cause cells to dislodge and migrate out of the collection area. Cells may also be lost during fixation as a result of the migration.

A sample chamber for large samples that provides a more even distribution of the sediment on the slide as well as better drainage and removal of the sample liquid left after centrifugation is needed.

SUMMARY OF THE INVENTION

According to the invention, it has been found that a sample in a sample receiving well holding up to about six milliliters of sample, can be effectively mixed prior to application to a microscope slide and applied substantially uniformly to the microscope slide by passing the sample from the sample receiving well into a sedimentation chamber, preferably into the top of the sedimentation chamber, which sedimentation chamber is substantially aligned with the centrifugal force applied to the sample during centrifugation. The top and bottom walls of the sedimentation chamber are substantially perpendicular to the microscope slide to ensure even cell distribution. The sides of the sedimentation chamber are also substantially perpendicular to the slide to maximize the volume of the sedimentation chamber even though this slightly misaligns the walls with the centrifugal force. However, this slight misalignment of the side walls has been found to be insignificant in practice and does not significantly distort the sediment distribution in the slide. The sedimentation chamber is at least as large as the sample receiving well so that all of the sample from the well can flow into and be received in the sedimentation chamber. It has been found that as the sample flows into and through the sedimentation chamber and against the microscope slide under centrifugal force, the sample and any portion thereof that has settled in the sample well becomes well mixed in the sedimentation chamber.

In one embodiment of the invention, the sample chamber is configured to attach to a cytocentrifuge rotor along a radial axis from the center of the cytocentrifuge and to extend along that radial axis. A sample receiving well is located at the inward end of the sample chamber (end toward the center) and communicates with the inner end of a sedimentation chamber by a sloped wall which extends upwardly and outwardly to a spillway separating the sample receiving well from the sedimentation chamber. A sample receiving well top includes a pipette opening so that a sample can be introduced into the sample receiving well from a pipette. The sample receiving well top also helps direct the sample over the spillway into the top of the sedimentation chamber. The sedimentation chamber opens at its outward end to a microscope slide removably positioned and held against the open outer end of the sedimentation chamber. A sealing material around the open end of the sedimentation chamber forms a seal between the sedimentation chamber and the microscope slide. The sample chamber and microscope slide are both removably attached to the rotor.

The sample well in the sample chamber is a cup shaped receiving receptacle having a wall that slopes upwardly and outwardly to the spillway so that as the rotor begins to spin, the sample in the sample well flows up the sloped wall by centrifugal force and over the spillway into the sedimentation chamber. The sample is collected in the sedimentation chamber against the microscope slide which forms the outward end of the sedimentation chamber. A vacant space is formed at the inward end of the sedimentation chamber. The centrifugal force created by the spinning of the sample chamber forces the sample against the microscope slide and the cells and/or other sediment material in the sample to flow through the sample liquid and be forced against the microscope slide. This force will generally bind the cells and sediment material to the slide and such material will remain on the slide when centrifugation stops and the liquid portion of the sample flows from against the microscope slide backwardly into the sedimentation chamber to level out by gravity in the sedimentation chamber.

To remove the sample liquid remaining in the sedimentation chamber after centrifugation stops, the sample chamber also includes at least one liquid removal chamber in communication with the sedimentation chamber to remove such sample liquid from the sedimentation chamber when centrifugation stops. Communication between the sample sedimentation chamber and the at least one liquid removal chamber is toward the inward end of the sedimentation chamber in the vacant space created in the sedimentation chamber during centrifugation so that sample is not removed from the sedimentation chamber during centrifugation, but only when centrifugation stops and the liquid portion of the sample flows backwardly within the sedimentation chamber toward the inward end of the sedimentation chamber. Communication between the sedimentation chamber and the at least one liquid removal chamber can be accomplished communication passage such that by rectangular gaps or holes and/or circular holes extending between the chambers. The location and configuration of the at least one liquid removal chamber will vary with the requirements and configuration of the cytocentrifuging device. Where there is room below the level of the sedimentation chamber, the at least one liquid removal chamber can be located below the sedimentation chamber so that the liquid portion of the sample can flow by gravity from the sedimentation chamber into the liquid removal chamber. With this configuration, the at least one liquid removal chamber can be filled with absorbent material to stabilize the fluid or simply contain the fluid in un-stabilized condition in the at least one liquid removal chamber. Where the configuration of the equipment does not allow the liquid removal chamber to be located below the sedimentation chamber, the at least one liquid removal chamber will contain absorbent material to absorb the sample fluid and draw it out of the sedimentation chamber and into the absorbent material in the liquid removal chamber.

The at least one liquid removal chamber can be one or more chambers located on the sides of the sedimentation chamber and extending upwardly from the bottom or floor of the sedimentation chamber with communication between the sedimentation chamber and the one or more liquid removal chamber at the bottom inward end of the sedimentation chamber. The liquid portion of the sample then flows from the sedimentation chamber into the one or more liquid removal chamber when centrifugation stops and the liquid flows backwards within the sedimentation chamber and toward the inward end of the sedimentation chamber so that the liquid is in communication with the communication between the sedimentation chamber and the one or more liquid removal chamber at the inward end of the sedimentation chamber. The one or more liquid removal chamber is filled with absorbent material so that the sample liquid from the sedimentation chamber is absorbed vertically upwardly into the absorbent material. As the liquid is absorbed by the absorbent material, more liquid flows into the one or more liquid removal chamber until all liquid is removed from the sedimentation chamber. It has been discovered that liquid removal is better than expected from the sedimentation chamber into the one or more vertical liquid removal chambers. Apparently the surface tension of the liquid is sufficient to pull the liquid across the horizontal floor of the sedimentation chamber into the one or more liquid removal chamber and absorbent material therein. The only remaining liquid in the sedimentation chamber is a few droplets at the interface between the sedimentation chamber and the microscope slide, primarily at the bottom of the sedimentation chamber.

With the liquid removed from the sedimentation chamber and held in the at least one liquid removal chamber, the sample chamber can be removed from the centrifuge and the microscope slide removed without spilling any of the sample liquid. If desired, before removal of the sample chamber and microscope slide from the centrifugation device, but after removal of the sample liquid from the sedimentation chamber, the sample adhered to the microscope slide can be subjected to secondary centrifugation to flatten out the cells on the microscope slide. This secondary centrifugation can be carried out since the sample liquid, which would otherwise interfere with the secondary centrifugation, is trapped in the at least one liquid removal chamber.

The last residual drops remaining at the point of contact of the chamber with the microscope slide are removed with the chamber by either physical collection or absorbent means at the slide contact. The absorbent means can be a collapsible foam seal between the sedimentation chamber and the microscope slide which expands and collects the droplets as the clamping pressure is released and the sedimentation chamber and microscope slide are separated, or an absorbent material can be provided in addition to the sealing means. In the latter case, the absorption material could contact the liquid droplets after the seal is released. The sealing means can also have an expandable lip that collects the droplets without actually absorbing them. Another type of seal includes an expandable lip with absorption material that collapses within the lip while compressed, but absorbs liquid droplets after compression and when the chamber is being removed. Another type of seal would include a silicone gasket and a strip of compressible absorbent material that overlaps the silicone gasket. The absorbent material would collapse during compression and not absorb liquid during centrifugation, but upon the release of compression, the absorbent material would decompress and absorb the droplets on the slide.

THE DRAWINGS

In the accompanying drawings, which show the best mode currently contemplated for carrying out the invention.

DETAILED DESCRIPTION OF THE ILLUSTRATED EMBODIMENT

The sample chamber of the invention is intended for use with a cytocentrifuge device where usually a plurality of sample chambers are removably secured to the rotor of the centrifuge device, each in association with a removably mounted microscope slide, so that cells or other sediment material in the sample in the sample chamber, upon centrifugation of the sample chamber and associated microscope slide, adhere to the microscope slide. After centrifugation, the microscope slide is removed from the cytocentrifuge rotor and the cells or other sediment materials adhered to the slide are then tested and evaluated in the usual manner. The invention will be described and is illustrated with an embodiment of the invention specifically configured to be mounted on a cytocentrifuge rotor of a cytocentrifuge device such as shown in U.S. Pat. No. 5,252,228, incorporated herein by reference, as manufactured by Wescor, Inc. of Logan, Utah under the trademark CYTOPRO. However, it should be realized that sample chambers with the inventive features described could be configured to mount on various other cytocentrifuge rotors.

Figure 10:
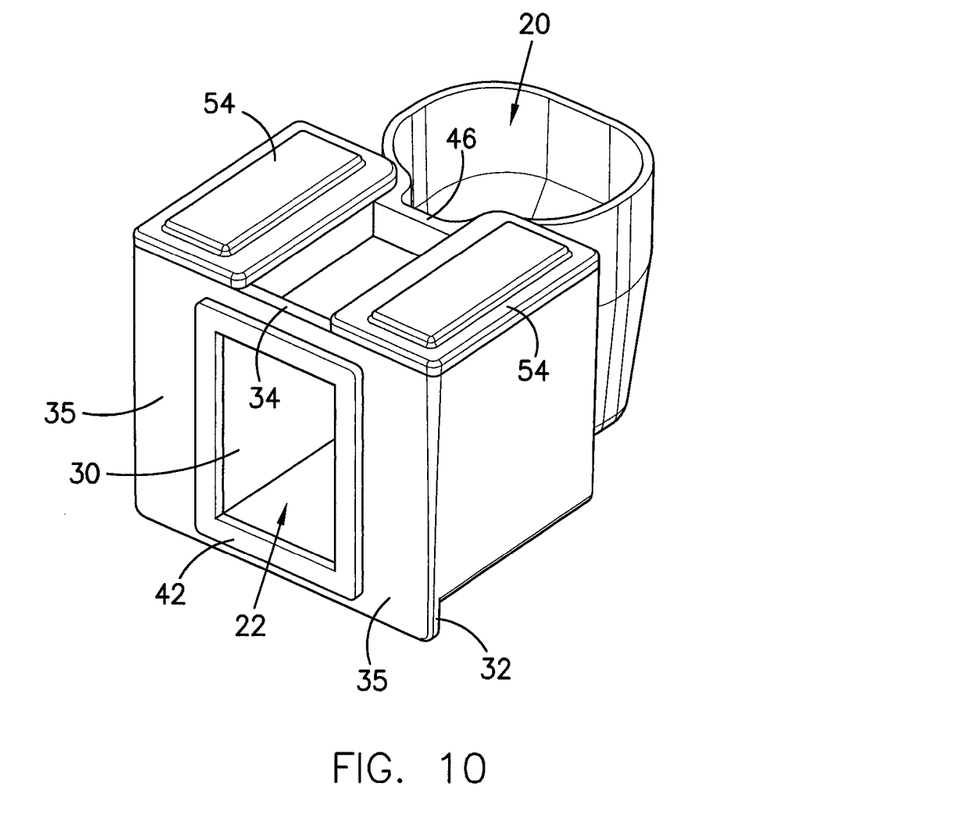
FIG. 10, a front right side perspective view of the sample chamber of FIG. 9.
Figure 11:
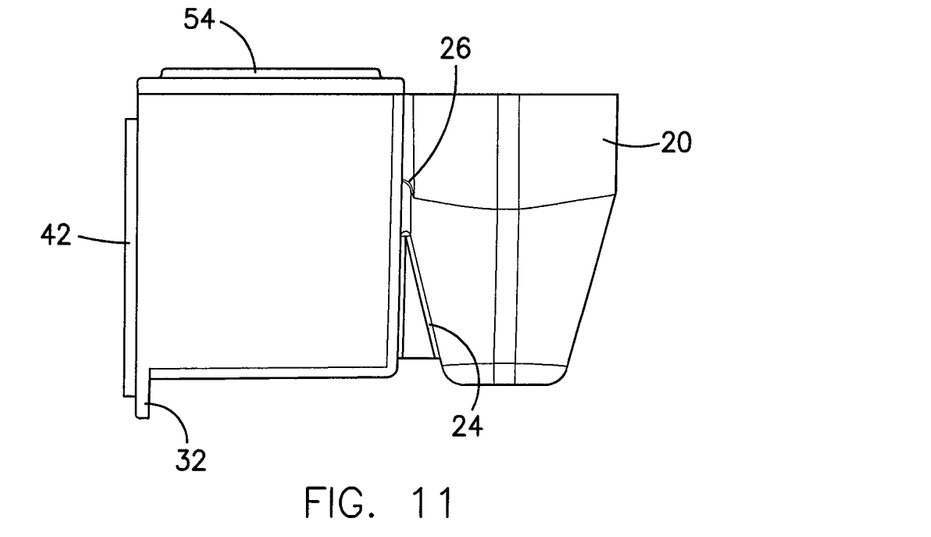
FIG. 11, a side view of the sample chamber.
Figure 12:
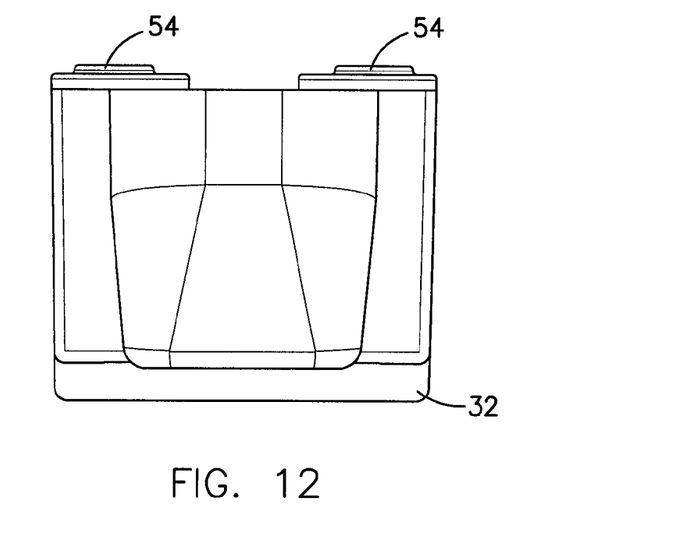
FIG. 12, a rear view of the sample chamber.

In the illustrated embodiment of the cytocentrifuge sample chamber of the invention, the sample chamber includes a sample well 20 which receives and holds the sample to be centrifuged prior to start of centrifugation and a sample sedimentation chamber 22. The sample well 20 and sample sedimentation chamber 22 are separated by a sloped sample well wall portion 24 with a spillway 26 at the top thereof which also forms the top of inner or rear sample sedimentation chamber wall 28. The front or outward end of sample sedimentation chamber 22 is open at opening 30. A bottom flange 32 extends along the front bottom of the sample chamber and extends along the bottom of opening 30 while a top flange 34 extends along the front top of the sample chamber and extends along the top of opening 30. Front walls 35, FIGS. 6, 7, and 10, extend along the sides of opening 30. Sample sedimentation chamber 22 also has opposite side walls 36, FIG. 4, a bottom wall 38, and a top wall 40, all of which, in this embodiment, are substantially perpendicular to the microscope slide surface. A sealing material 42, FIGS. 6, 10, and 13-16, surrounds the opening 30. When the sample chamber is positioned in a cytocentrifuge, the opening 30 is positioned adjacent a microscope slide upon which the cells or other sedimentation material in the sample are to be deposited during the centrifugation. Sealing material 42 prevents leakage of the sample between the sample chamber and the microscope slide. A sample well top 44 fits over sample well 20 and abuts rear top flange 46 to provide a closed top between the sample well 20 and sedimentation chamber 22. A pipette port 47 in top 44 allows sample loading of the sample well with a pipette, and also serves as a vent hole.

Figure 4:
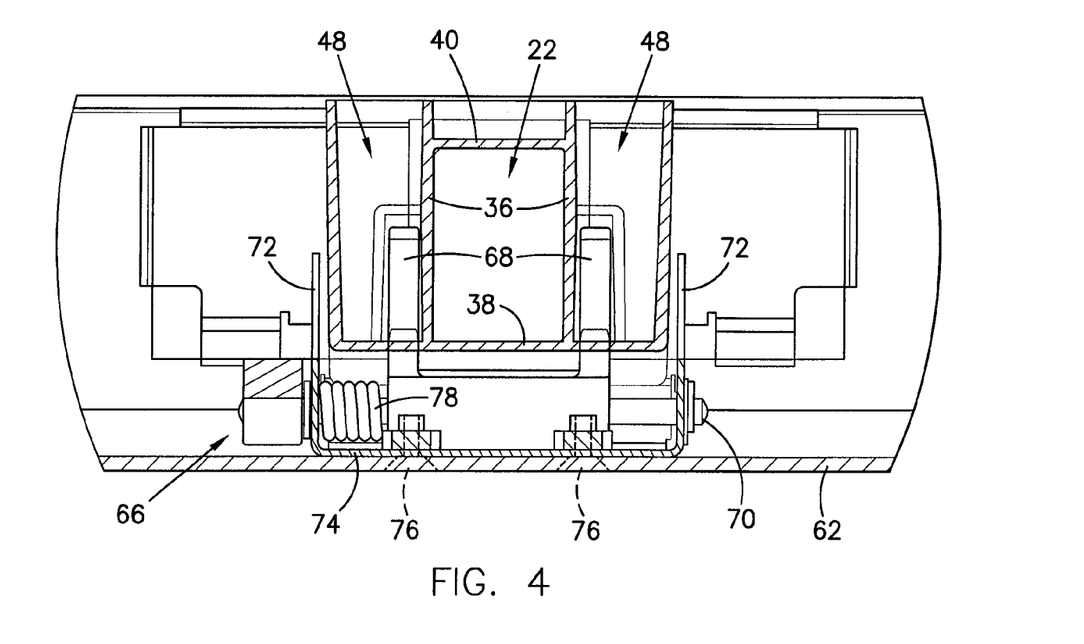
FIG. 4, a vertical section of the sample chamber mounted on the rotor.
Figure 5:
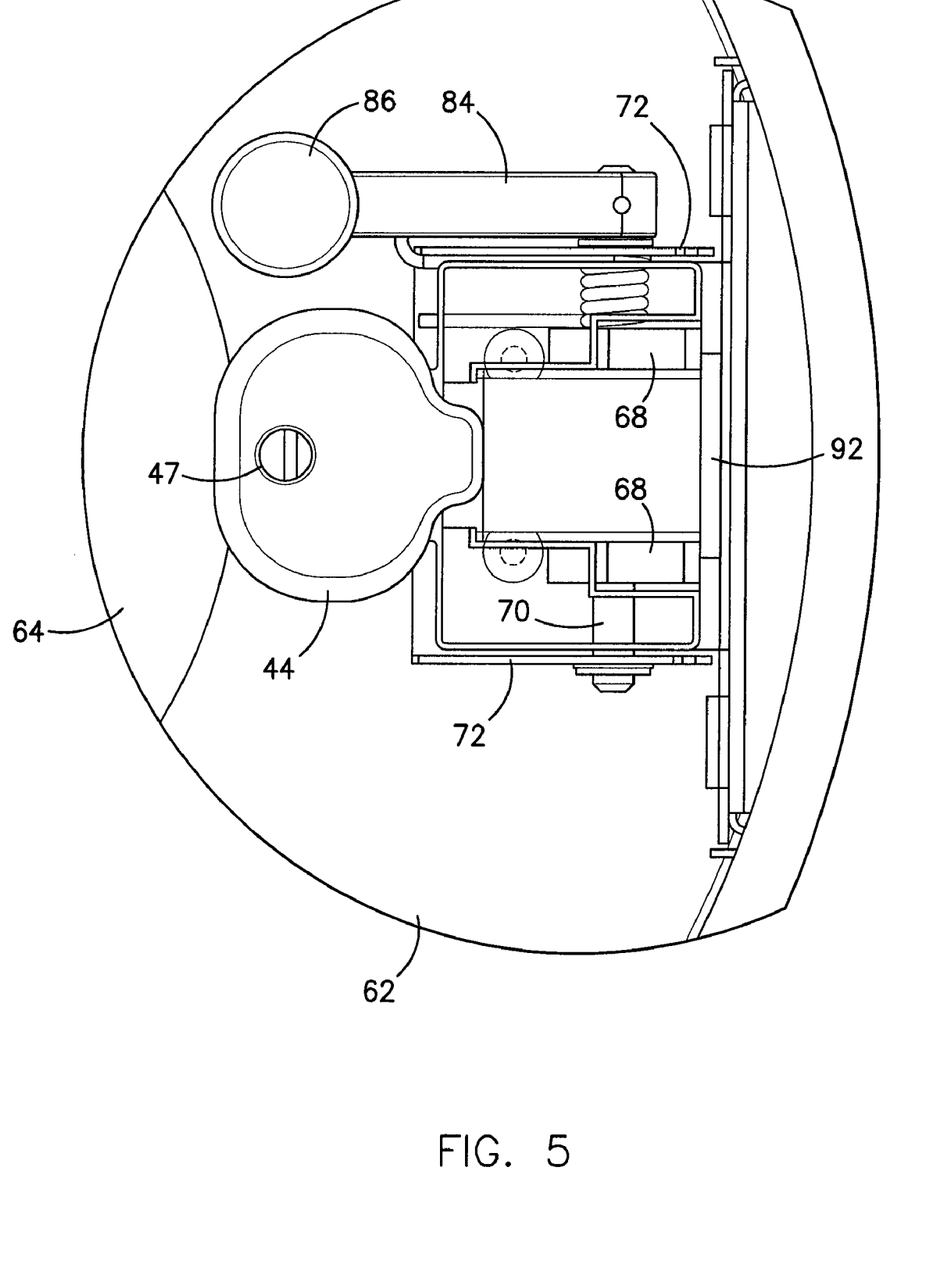
FIG. 5, a top view of the sample chamber mounted on the rotor.
Figures 6, 7:
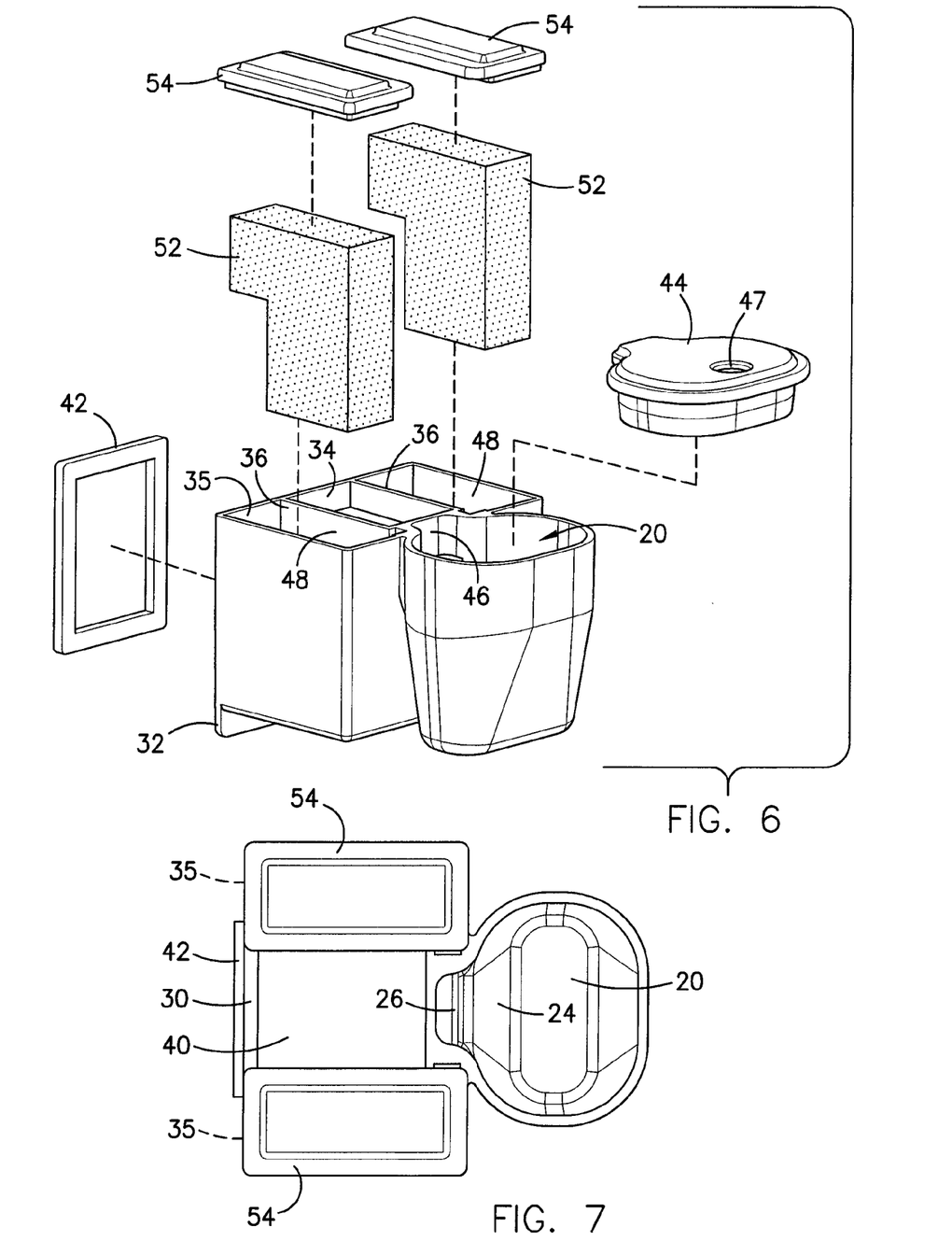
FIG. 6, a perspective assembly view of the sample chamber.
FIG. 7, a top view of the sample chamber showing the liquid removal chamber tops in place and the sample well top removed.
Figure 13:
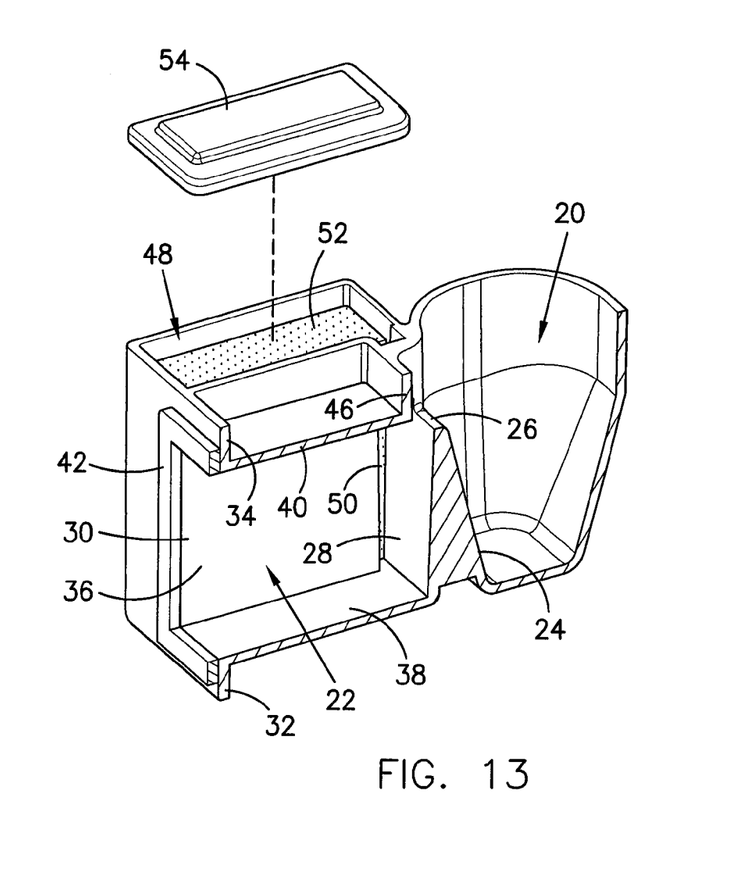
FIG. 13, a perspective vertical section of the sample chamber.

Liquid removal chambers 48, FIGS. 4, 6, and 13, are positioned along opposite sides of the sedimentation chamber 22, separated therefrom by sedimentation chamber side walls 36. A removal gap or opening 50, FIG. 13, extends through sample sedimentation chamber side walls 36 adjacent sedimentation chamber rear wall 28 to connect the liquid removal chambers 48 with the sedimentation chamber 22 to allow fluid to flow from the sample sedimentation chamber 22 into the liquid removal chambers 48. The bottom of gaps 50 should be even with or below sedimentation chamber bottom wall 38 so that all of the sample liquid in the sedimentation chamber 22 can flow into the liquid removal chambers 48, but the gaps 50 do not have to extend to the top of the sedimentation chamber. In the illustrated embodiment, which is configured to fit a particular cytocentrifuge rotor, the liquid removal chambers 48 are side-by-side with the sample sedimentation chamber 22 and the bottoms of the liquid removal chambers 48 are aligned with the bottom 38 of the sample sedimentation chamber 22. The liquid removal chambers extend upwardly from the bottom of the sedimentation chamber. For this particular arrangement, absorption material 52, FIG. 6, is positioned in the liquid removal chambers 48 to absorb the sample liquid as it flows from the sample sedimentation chamber 22 into the liquid removal chambers 48. The absorption material 52 is selected, sized, and positioned in the liquid removal chambers to absorb substantially all of the sample liquid expected to fill the sample sedimentation chamber 22 during use of the sample chamber. Thus, the absorption material 52 has the capacity to absorb all of the sample liquid expected to fill the sedimentation chamber to thereby completely empty the sample sedimentation chamber 22 of sample liquid after centrifugation is completed and stopped. With the arrangement shown, where the bottoms of the liquid removal chambers are aligned with the bottom of the sedimentation chamber, the bottom of the absorption material 52 should be in contact with the bottom of the liquid removal chamber to be able to remove substantially all of the sample liquid. In other arrangements of the liquid removal chamber with respect to the sedimentation chamber, where at least some vertical movement of the sample liquid is desired, the absorption material should extend downwardly in the liquid removal chamber at least to the level of the bottom of the sedimentation chamber. Each liquid removal chamber 48 has a liquid removal chamber top 54 which fits over the top of a liquid removal chamber 48.

Figure 1:
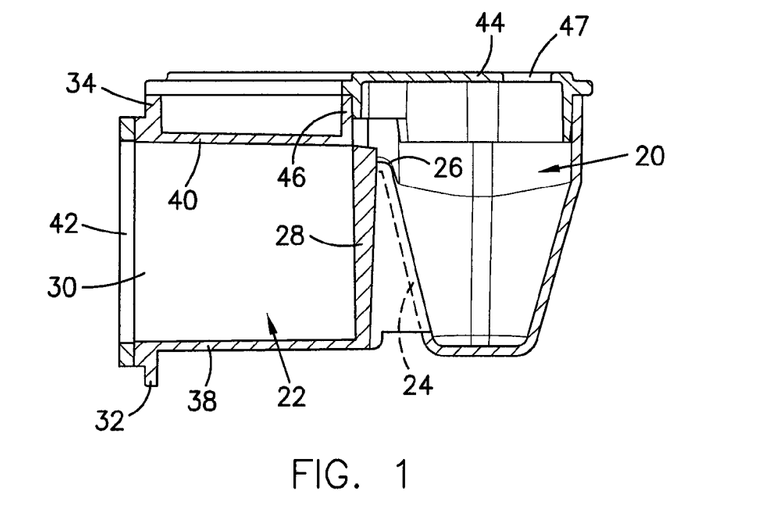
FIG. 1 is a vertical section through an example sample chamber of the invention.
Figure 2:
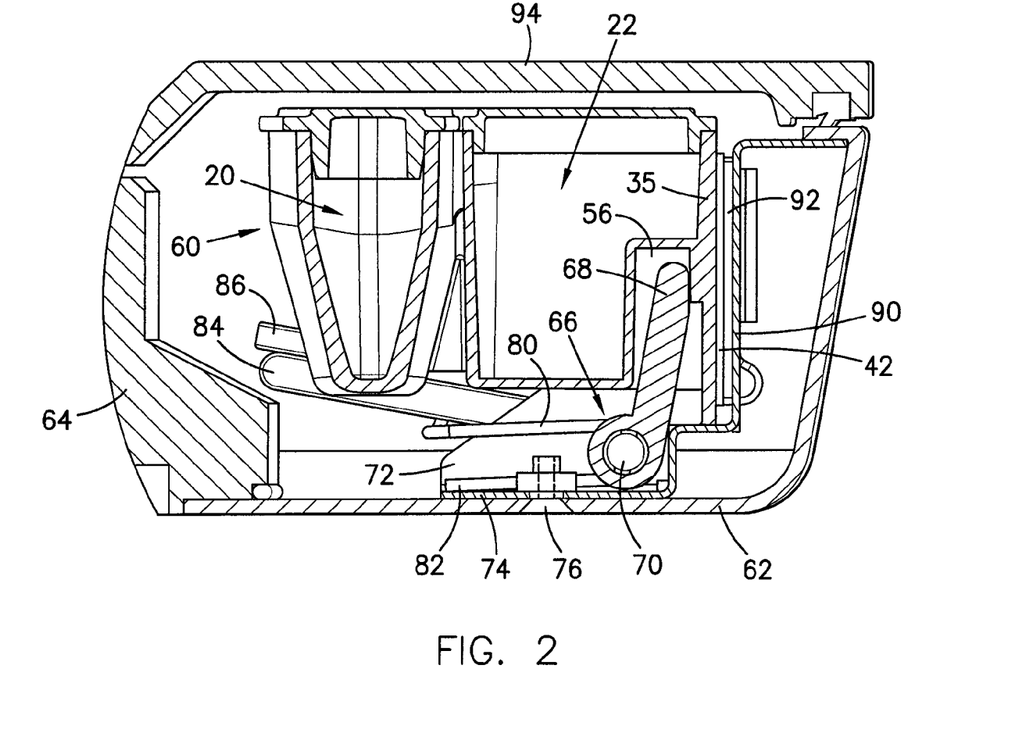
FIG. 2, a vertical section through the sample chamber mounted on a rotor of a cytocentrifugation device shown in fragmentary section.
Figure 3:
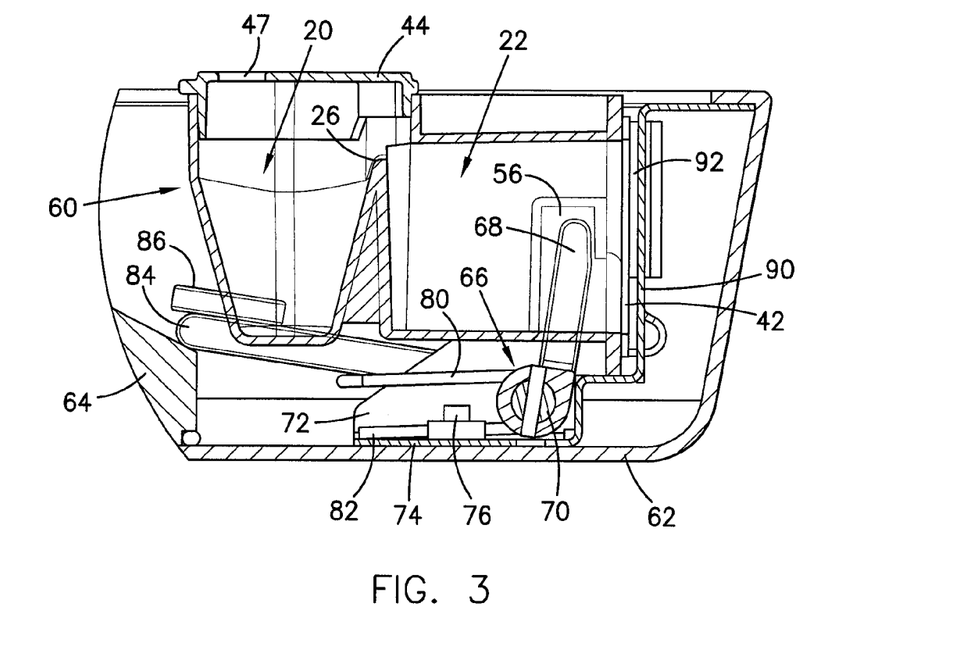
FIG. 3, a vertical section similar to that of FIG. 2.
Figure 8:
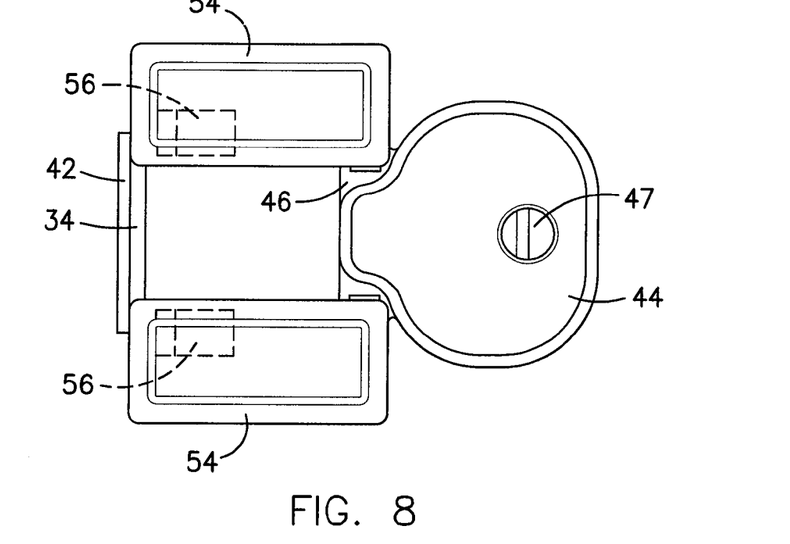
FIG. 8, a top view of the sample chamber with the liquid removal chamber tops in place and the sample well top in place and showing the mounting finger chambers in broken lines.
Figure 9:
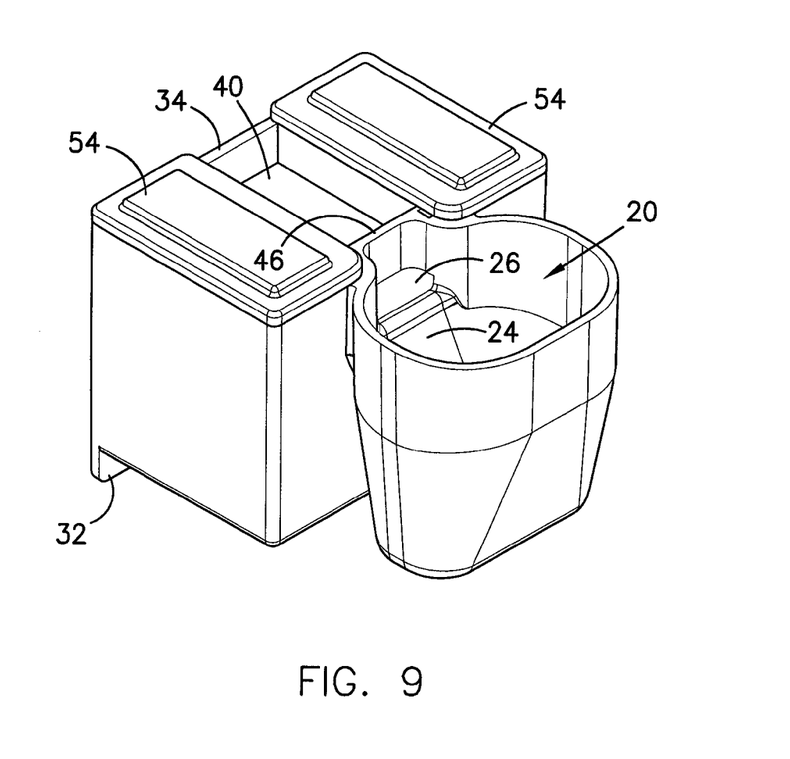
FIG. 9, a rear right side perspective view of the sample chamber showing the removal chamber tops in place and the sample well top removed.

For the particular embodiment shown, the sample chamber also includes centrifuge rotor mounting arm receiving compartments 56, FIGS. 2 and 8, which open to the bottom of the sample chamber to receive clamping arms of a centrifuge rotor.

In order to use the sample chamber of the invention, the sample chamber must be mounted on a cytocentrifuge rotor in a cytocentrifuge apparatus. As indicated, the illustrated embodiment is configured to be mounted on a cytocentrifuge rotor of a cytocentrifuge such as shown in U.S. Pat. No. 5,252,228 as manufactured by Wescor, Inc. of Logan, Utah under the trademark CYTOPRO. As shown in FIGS. 2-5, the sample chamber 60 of the invention is mounted on a cytocentrifuge rotor 62 which is removably and replaceably mounted for rotation on a centrifuge machine, not shown, by central rotor fitting 64 which fits over a rotating hub, not shown, of the centrifuge machine. The rotor 62 is normally configured to receive a plurality of sample chambers 60 extending around the rotor and each aligned along a radially extending axis from the center of the rotor. What has been referred to herein as the rear, inward, or inner end of the sample chamber faces the center of the rotor and what has been referred to as the front, outward, or outer end of the sample chamber faces outwardly from the center of the rotor.

A clamping means 66, FIGS. 2-5, for each sample chamber to be mounted to rotor 62 is secured to rotor 62 and includes a pair of clamping arms 68 fixed on shaft 70 that is rotatably inserted in and between upstanding members 72, respectively, of base plate 74 that is secured to rotor 62 by screw 76. Clamping arms 68 are normally held in clamping position by a coil spring 78 on shaft 70 having respective ends 80 and 82 that bear against an arm 84 which is fixedly secured to one end of shaft 70 and base plate 74 to urge clamping arms 68 outwardly. For relieving clamping pressure, arm 84 has a handle 86 for manipulation by a user to move arm 84 against the force of spring 78 to rotate clamping arms 68 inwardly when it is desired to remove a sample chamber 60 from the rotor 62 or to secure a sample chamber 60 to the rotor 62. The clamping means also includes a microscope slide holder 90 which receives a microscope slide 92 removably inserted into the slide holder 90. Clamping arms 68, when received in centrifuge rotor mounting arm receiving compartments 56 of the sample chamber and when rotated outwardly toward the microscope slide holder 90 by spring 78, force the sample chamber and the open end of the sedimentation chamber therein against microscope slide 92 and hold the sample chamber on the centrifuge rotor.

To use the sample chamber of the invention, such as sample chamber 60 of FIGS. 2-5, a user operates handle 86 to move arm 84 to rotate shaft 70 and clamping arms 68 inwardly. A microscope slide 92 is mounted in slide holder 90 and sample chamber 60 is placed on rotor 62 with clamping arms 68 extending into sample chamber centrifuge rotor mounting arm receiving compartments 56 as shown in FIG. 2. Handle 86 is released to allow clamping arms 68 to rotate into clamping position against sample chamber front end walls 35. This forces the sample chamber 60 outwardly against microscope slide 92 so that sealing material 42 is against microscope slide 92 and sedimentation chamber opening 30 is adjacent microscope slide 92. In this position, sample chamber 60 is held in position on rotor 62. The sample from which cells or other sediment material is to be applied to the microscope slide may be loaded into sample well 20 either prior to securing the sample chamber to the rotor or after securing the sample chamber to the rotor. For the embodiment shown, the sample is loaded into sample well 20 through a pipette inserted through pipette opening 47 in sample well cover 44. If the sample is loaded into the sample well prior to securement of the sample chamber to the rotor, care must be used in securing the sample chamber to the rotor not to tip the sample chamber to allow the sample to flow from the sample well into the sedimentation chamber.

Once all sample chambers to be secured to the rotor are secured to the rotor and the sample wells of all sample chambers are loaded with samples, a rotor cover 94 is secured in place over the rotor. The centrifuge device is then operated to rotate the rotor at a desired speed for a desired time. As the rotor begins to rotate, the sample in the sample well 20 begins to flow up the sloped well end wall 24 and flows over the spillway 26 into the sample sedimentation chamber 22. At first, as the rotor begins to spin, the sample flowing over the spillway 26 may fall by gravity downwardly into the sample sedimentation chamber 22 as well as outwardly, but as the speed increases, the sample will flow primarily outwardly from the spillway 26. The sample flowing from the sample well 20 into the sample sedimentation chamber 22 will flow by centrifugal force outwardly against microscope slide 92, which, because of opening 30, will form the outer end of the sample sedimentation chamber 22. The cells and other sediment components of the sample will be forced by centrifugal force through the liquid components of the sample through opening 30 and against the surface of the microscope slide 92 and will adhere to the surface of the microscope slide 92. The sample sedimentation chamber 22 is larger than the expected sample volume. The sample will all collect at the outward portion of the sample sedimentation chamber 22 away from the inward end of the sample sedimentation chamber 22 leaving a vacant space at least a distance equal to the width of the removal gap 50 at the inner end of the sample sedimentation chamber. Thus, during centrifugation, none of the sample will flow through the removal gap 50. This is achieved in the equipment described in U.S. Pat. No. 5,252,228 with high acceleration. After centrifugation for the desired time, centrifugation will stop and the sample liquid, which has been held by centrifugal force at the outward end of the sample sedimentation chamber 22 against the microscope slide 90, will flow backwardly within the sample sedimentation chamber and will tend to orientate horizontally by gravity in the sample sedimentation chamber 22. The liquid in the sedimentation chamber 22 will flow into the previously vacant space adjacent sedimentation chamber inner wall 28. However, it has been found that most of the sediment material adhered to the microscope slide will remain adhered to the slide. The portion of the sample that flows back to the rear of the sedimentation chamber (the vacant space), primarily the liquid components of the sample, will flow through the removal gaps and into the liquid removal chambers and will be absorbed by the absorbent material in the liquid removal chambers. This empties the sample sedimentation chamber 22 of sample liquid. At this point, with the sample sedimentation chamber 22 empty, the centrifuge apparatus can be operated to rotate the rotor for a secondary centrifugation or the sample chamber can be removed from the rotor without flow of material from the sample sedimentation chamber 22 onto the rotor and possibly onto the user to contaminate the rotor and user. During any secondary centrifugation, the cells and/or other materials adhered to the slide during the initial centrifugation are further flattened and further adhered to the microscope slide. If the secondary centrifugation is used, the sample chamber and microscope slide is removed from the rotor after such secondary centrifugation, again without contamination of the rotor or the user.

The spilling of the sample over the spillway from the sample well into the sedimentation chamber during centrifugation has been found to be turbulent and it has been found that substantially even distribution of the sample takes place. Even though the cells and other sediment material in the sample well may settle to the bottom of the well and spill over into the sedimentation chamber unevenly because the lighter fluid may spill over first, the sample is mixed in the chamber and a good even deposition of the material on the microscope slide is obtained. A test showing that mixing takes place was performed by putting a blue dye in the bottom of the sample well and putting water over the dye so the dye remained in the bottom of the well as a band. The rotor was started with the top of the chamber open and the chamber was observed using a strobe light. It was observed that good mixing took place and a homogeneous dye-water mixture was achieved. In additional testing to verify the mixing adequacy of the sample chamber, 6 ml samples of buccal cells were placed in the sample wells. The cytocentrifuge was operated in normal manner to centrifuge the samples. Observation of the cells as deposited on the microscope slides showed even distribution of cells throughout the collection area on the microscope slide.

When centrifugation is completed, the spinning of the rotor slows down and stops. The sample liquid flows from against the microscope slide into the vacant space in the sedimentation chamber and through the removal gap or opening into the liquid removal chamber or chambers. It has surprisingly been found that, probably due to the surface tension of the sample liquid, the absorption material 52 in the liquid removal chambers is able to pull substantially all of the sample liquid from the sedimentation chamber 22. Normally, the only remaining liquid in the sedimentation chamber is a few droplets at the interface between the sedimentation chamber and the microscope slide, primarily at the bottom of the sedimentation chamber. Thus, it has been found that the absorption material 52 in the liquid removal chambers, even though located away from the sedimentation chamber-microscope interface, is effective to remove substantially all of the sample liquid from the sedimentation chamber and from the microscope slide when centrifugation is completed and stopped. The location of the interconnection or communication between the sedimentation chamber and the liquid removal chambers near the inner wall of the sedimentation chamber where the vacant space is formed in the sedimentation chamber during centrifugation, substantially prevents any removal of the sample from the sedimentation chamber to the liquid removal chamber before or during centrifugation, and only allows removal of the sample liquid after centrifugation of the sample and deposition of the sediment material in the sample on the microscope slide is completed. Thus, maximum sediment material is deposited on the slide.

Figure 14:
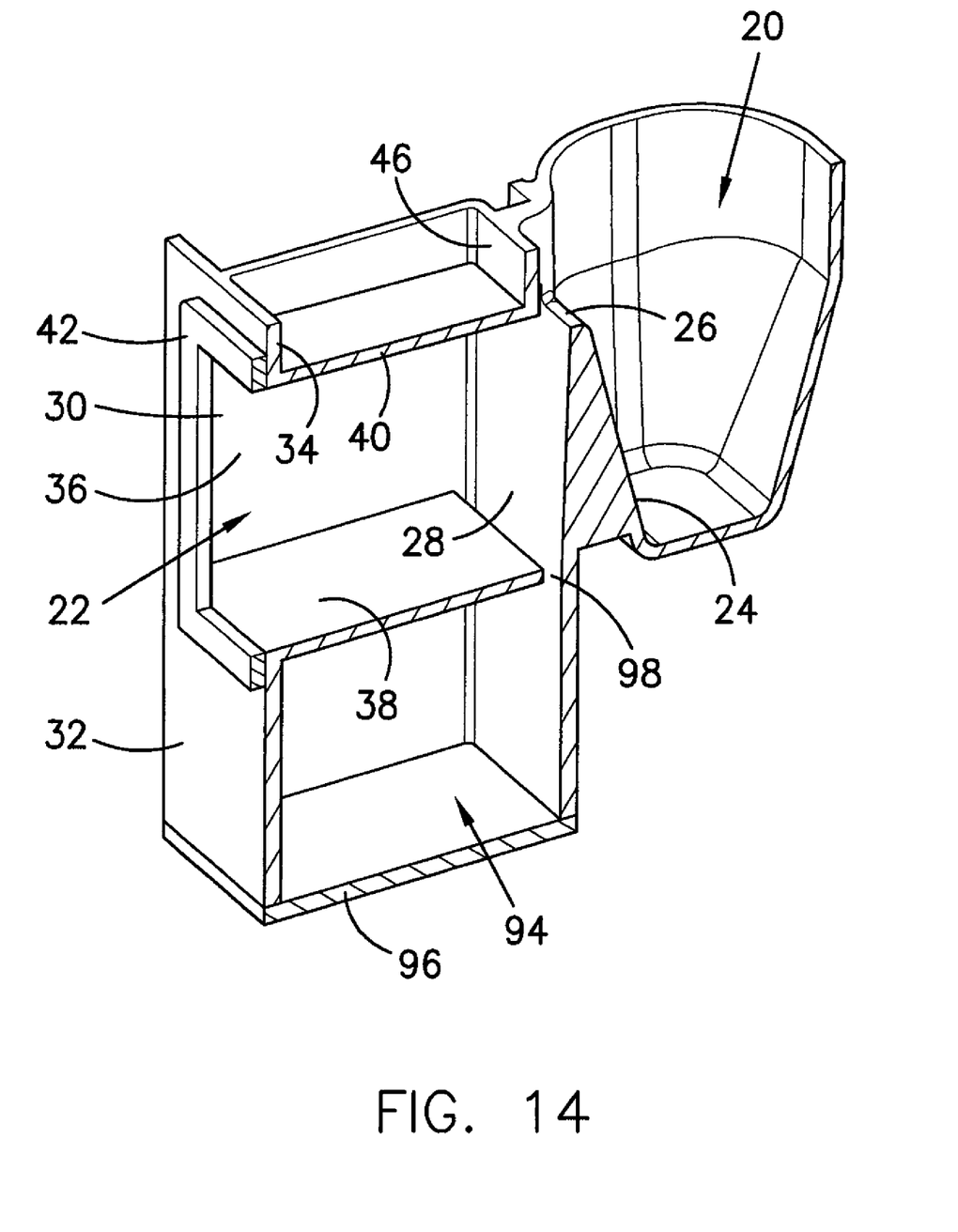
FIG. 14, a perspective vertical section similar to that of FIG. 13 showing a different embodiment of a liquid removal chamber in the sample chamber.

While various absorbent materials may be used in the liquid removal chambers to absorb the sample liquid in the sedimentation chamber after centrifugation, absorbent foam, such as open cell polyester, polyureathane, and polyvinyl alcohol foam has been found to work well. Cellulosic material can also be used for the absorbent material and absorbs well, but such material can produce fibers which may get into the sedimentation chamber and interfere with the sample on the microscope slide.

Where the particular cytocentrifuge device with which the sample chamber is to be used will allow it, the sample chamber of the invention may be configured with the liquid removal chamber positioned below the sample sedimentation chamber, an example of which is shown in FIG. 14. In the embodiment of FIG. 14, rather than liquid removal chambers 48 being positioned on opposite sides of the sedimentation chamber 22 and extending upwardly from the level of the sedimentation chamber floor 38 so that sample liquid removed from the sedimentation chamber has to be raised vertically from the sedimentation chamber as shown in prior Figures, a liquid removal chamber 94 is formed by extensions of sedimentation chamber rear or inner wall 28, bottom flange 32, and opposite side walls 36 below sedimentation chamber floor or bottom wall 38 to be closed by liquid removal chamber floor or bottom wall 96. Sedimentation chamber floor 38 does not extend all of the way to sedimentation chamber rear or inner wall 28 so as to leave a gap or opening 98 at the inner end of the sedimentation chamber adjacent sedimentation chamber rear or inner wall 28 to provide communication between the sedimentation chamber 22 and the liquid removal chamber 94. Gap or opening 98 connecting the sedimentation chamber and the liquid removal chamber is positioned at the inner end of the sedimentation chamber where the vacant space is formed during centrifugation by reason of the sample in the sedimentation chamber being forced by centrifugal force during centrifugation against the outer end of the sedimentation chamber formed by the microscope slide. Thus, the sample does not flow through gap 98 as it flows from sample well 20 over spillway 26 and is forced toward the outer end of the sedimentation chamber against the microscope slide during centrifugation, but must wait until centrifugation is completed and stopped before it can flow backwardly in the sedimentation chamber toward the inner wall 28 into the previously vacant space to flow through gap 98 into the liquid removal chamber 94.

In this embodiment, where the liquid removal chamber is located entirely below the sedimentation chamber, flow of sample liquid from the sedimentation chamber through gap 98 into liquid removal chamber 94 may take place entirely by gravity as opposed to absorption as in the prior embodiment described. However, to ensure that substantially all of the sample liquid will flow from the sedimentation chamber 22 into the liquid removal chamber 94 without leaving puddles on the sedimentation chamber floor, it may be advantageous to still provide absorbent material in the liquid removal chamber. In such instance, the absorbent material should extend through gap 98 to the top or slightly above the top of the gap 98 so that it will draw the sample liquid across the sedimentation chamber floor into the liquid removal chamber. Whether or not such absorbent material is needed will depend upon the configuration of the sedimentation chamber floor and the opening between the sedimentation chamber and the liquid removal chamber.

Once the sample liquid is removed from the sedimentation chamber into the liquid removal chamber, the sample chamber can then be subjected to a secondary centrifugation, if desired, wherein the removed sample liquid will remain in the liquid removal chamber 94 as located below the sedimentation chamber and being forced toward the closed outer end of the liquid removal chamber away from gap 98, or the sample chamber can be removed from the cytocentrifuge device with the sample liquid remaining by gravity in the liquid removal chamber 94. Even if absorbent material is not required to draw substantially all of the sample liquid from the sedimentation chamber for particular sedimentation chamber configurations, absorbent material may be desired to stabilize the sample liquid in the liquid removal chamber. In such case, absorption material can be provided in the liquid removal chamber, but such absorption material does not need to extend through the opening communicating with the sedimentation chamber. The absorption material in the liquid removal chamber will prevent the liquid in the liquid removal chamber from sloshing around and from possibly splashing up through gap 98. It will also prevent the liquid from running out or splashing out through gap 98 if the sample chamber is tipped or moved rapidly during removal from the cytocentrifuge device.

While embodiments of the invention have been shown with liquid removal chambers along side the sedimentation chamber and below the sedimentation chamber, the liquid removal chamber or chambers could be located partially below and partially alongside the sedimentation chamber in any desired arrangement to fit particular cytocentrifugation devices or for other reasons.

While various sealing materials can be used around the sedimentation chamber opening against the microscope slide to prevent leakage, it has been found that a compressible absorbent or semi-absorbent material provides certain advantages. As used herein, both absorbent and semi-absorbent materials will be referred to as absorbent materials. A compressible absorbent material works well as the sealing material and can improve results by absorbing the residual droplets of fluid from the microscope slide surface when centrifugation stops and sample liquid has been withdrawn from the sedimentation chamber into the sample removal chamber or chambers. During clamping and centrifugation, the sample chamber is forced against the microscope slide with enough force to compresses a compressible absorbent seal material between the end of the sedimentation chamber and the microscope slide so it can absorb only a very limited amount of liquid, if any. When centrifugation stops, and particularly when the sample chamber is being removed from the rotor thereby relieving the clamping spring pressure forcing the sample chamber against the microscope slide and compressing the seal, the seal expands slightly and absorbs the sample liquid remaining on the microscope slide around the opening (the edges) of the seal. When stopping centrifugation, and after removal of the sample liquid from the sedimentation chamber-microscope slide interface, it has been found that the remaining sample liquid is usually in the form of droplets around the sides of the opening from the sedimentation chamber to the microscope slide, with the biggest droplets being at the bottom. As the seal material expands, these droplets are absorbed. It has been found that it can take up to about one minute for the droplets to be absorbed. This is found by taking the slide out immediately upon stopping the rotation and finding droplets around the edge of the sample deposition on the slide. The seal material against the slide is another surface, additional to the slide, for the droplets to adhere. Due to the surface tension of the fluid, the droplets gather at the edges of the seal. The absorbent foam in the removal chambers, or the gravity flow of sample liquid into a liquid removal chamber, cannot overcome this tensional additional force on these droplets. Therefore, they remain on the microscope slide along the sealing material. However, these droplets can be absorbed by an absorbent sealing material. A foam material, such as a closed cell vinyl foam having about a 10% by volume absorption capacity, has been found satisfactory. This material may be provided in a strip that extends around the periphery of the open end of the sedimentation chamber. Other foam materials and other sealing materials and sealing material configurations, can also be used. For example, the sealing material 42 may be a strip of other closed cell foam material, a strip of open cell collapsible foam material, a strip of silicone material, absorbent material enclosed in other sealing material, or combinations thereof, which can prevent leakage of the sample liquid around the sample chamber during centrifugation.

Figure 15A:
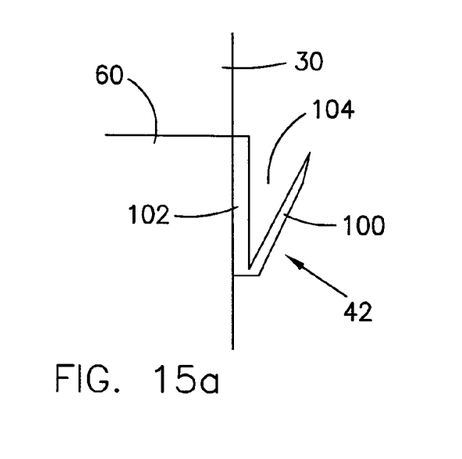
FIG. 15a, a vertical section through an alternate embodiment of seal between the sample chamber and the microscope slide with the seal in expanded condition as spaced from the microscope slide.
Figure 15B:
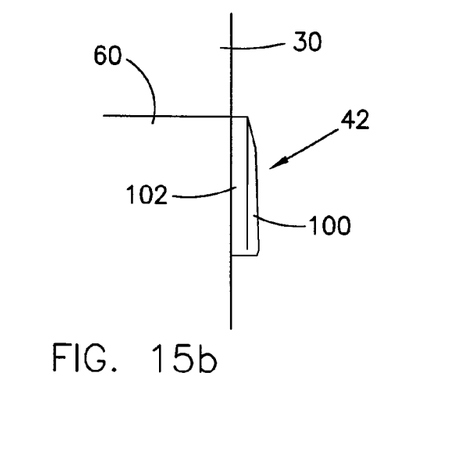
FIG. 15b, a similar vertical section through the seal of FIG. 14a, showing the seal in compressed condition as it would be between the sample chamber and microscope slide during centrifugation.
Figure 16A:
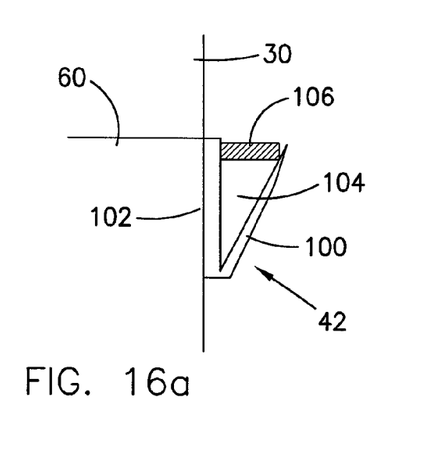
FIG. 16a, a vertical section through a further alternate embodiment of seal between the sample chamber and the microscope slide with the seal in expanded condition as spaced from the microscope slide.
Figure 16B:
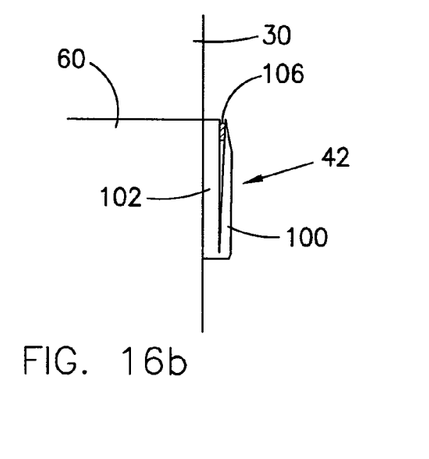
FIG. 16b, a similar vertical section through the seal of FIG. 15a, showing the seal in compressed condition as it would be between the sample chamber and microscope slide during centrifugation.
Figure 17A:
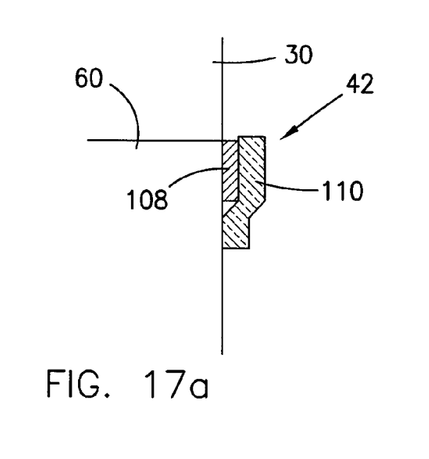
FIG. 17a, a vertical section through a still further alternate embodiment of seal between the sample chamber and the microscope slide with the seal in expanded condition as spaced from the microscope slide.
Figure 17B:
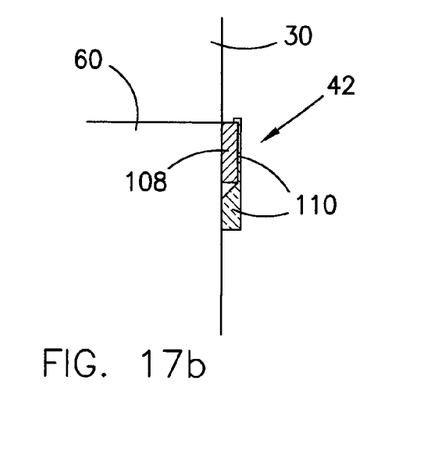
FIG. 17b, a similar vertical section through the seal of FIG. 16a, showing the seal in compressed condition as it would be between the sample chamber and microscope slide during centrifugation.

Rather than merely a strip of foam material, the sealing material may be in a configuration where there is a lip 100, FIGS. 15*a* and 15*b*, normally extending outwardly at an angle to a base 102 secured to the sample chamber 60, FIG. 15*a*, to form an open channel 104 between the base and lip. When pressed against the microscope slide, the lip 100 is pressed against the base 102 as shown in FIG. 15*b*. When the clamping pressure of the sample chamber 60 against the microscope slide is released, lip 100 opens to its normally open position shown in FIG. 15*a*. As lip 100 opens, it draws the liquid droplets along its edge into the opening 104 between the base and lip. If desired, a collapsible or compressible absorbent material 106, FIGS. 16*a* and 16*b*, such as a foam material, can be positioned in opening 104 between lip 100 and base 102. In such instance, with clamping pressure applied between the sample chamber and the microscope slide, lip 100 is forced against base 102 with the compressible material compressed therebetween as shown in FIG. 16*b*. As pressure is released, lip 100 opens and compressible material 106 expands to draw and absorb liquid droplets into the expanding compressible material. The sealing material 42 could also include a strip of nonabsorbent sealing material 108, FIGS. 17*a* and 17*b*, such as a strip of silicone sealing material, overlapped with a strip of compressible absorbent material 110. In this embodiment, with clamping pressure applied between the sample chamber and the microscope slide, compressible material 110 is compressed against sealing material 108 and sample chamber 60 as shown in FIG. 17*b*. As pressure is released, compressible material 110 expands to draw and absorb liquid droplets into the expanding compressible material.

While the sample chamber of the invention can be made in various sizes, a sample well which can hold up to about six milliliters of sample and a sedimentation chamber having about a seven milliliter volume should be satisfactory for most testing currently contemplated. With this large volume sample chamber, a large open area against the microscope slide provides a large sample on the slide to be observed. The sample provided by the illustrated embodiment is about 0.58 by 0.84 inches.

The invention also includes the method for removing sample fluid from a sample sedimentation chamber after centrifugation to deposit cells or other sedimentation onto a microscope slide, by providing a sedimentation chamber of larger volume that the sample receiving well so that a vacant space is formed at the inner end of the sedimentation chamber when the sample from the sample receiving chamber flows by centrifugal force into the sedimentation chamber and is forced against the microscope slide, and by providing liquid removal chambers communicating with the vacant space so that no sample is removed until centrifugation stops and fluid flows back into the vacant space in the sedimentation chamber so is then removed from the sedimentation chamber. The method further includes providing absorbent material in the liquid removal chambers to absorb the liquid sample from the sedimentation chamber and to draw the liquid sample from the sedimentation chamber into the liquid removal chambers. The method also additionally includes providing an absorption material around the sedimentation opening of the sedimentation chamber to remove fluid droplets from the microscope slide at the end of centrifugation.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. A sample chamber for use in a cytocentrifuge device for receiving and distributing a sample containing sediment material to be deposited onto a microscope slide during cytocentrifugation, comprising:

a sample receiving well for receiving and holding the sample prior to centrifugation;

a sedimentation chamber comprising an outer open sedimentation end, an inner end, and a floor, the open sedimentation end adapted to be positioned adjacent a microscope slide allowing the sample to collect in the sedimentation chamber toward the open sedimentation end allowing sediment material from a sample in the sedimentation chamber to contact the microscope slide during centrifugation and forming a vacant space at the inner end of the sedimentation chamber during centrifugation;

a passage from the sample receiving well into the sedimentation chamber whereby sample will flow under centrifugal force from the sample receiving well into the sedimentation chamber during centrifugation;

a liquid removal chamber in communication with the vacant space in the sedimentation chamber during centrifugation to remove sample liquid from the sedimentation chamber when centrifugation stops and sample liquid flows into the vacant space;

a communication passage between the liquid removal chamber and the sedimentation chamber, opening into the sedimentation chamber adjacent the inner end and floor of the sedimentation chamber; and     a sealing material surrounding the open end of the sedimentation chamber for sealing against the microscope slide when the sample chamber is positioned in a cytocentrifuge device against a microscope slide.

2. The sample chamber for use in a cytocentrifuge device according to claim 1, wherein the sedimentation chamber further comprises an inner end wall and side walls, and wherein the communication passage opening into the sedimentation chamber extends through at least one of the inner end wall and the side walls.

3. The sample chamber for use in a cytocentrifuge device according to claim 2, wherein the liquid removal chamber includes an absorbent material to absorb the sample liquid and draw sample liquid from the sedimentation chamber.

4. The sample chamber for use in a cytocentrifuge device according to claim 3, wherein there are two liquid removal chambers, each chamber being located on opposing sides of the sedimentation chamber.

5. The sample chamber for use in a cytocentrifuge device according to claim 4, wherein the sedimentation chamber floor is substantially horizontal when the sample chamber is positioned in the cytocentrifuge device.

6. The sample chamber for use in a cytocentrifuge device according to claim 4, wherein a sample of a maximum volume is expected in the sedimentation chamber, and wherein the liquid removal chambers collectively have a volume greater than the maximum sample volume.

7. The sample chamber for use in a cytocentrifuge device according to claim 4, wherein the liquid removal chambers have removal chamber floors substantially aligned with the sedimentation chamber floor, and wherein the liquid removal chambers extend upwardly from the removal chamber floors.

8. The sample chamber for use in a cytocentrifuge device according to claim 7, wherein the absorbent material draws the sample liquid upwardly in the liquid removal chamber and keeps the sample liquid in the liquid removal chamber during any subsequent centrifugation.

9. The sample chamber for use in a cytocentrifuge device according to claim 1, wherein the liquid removal chamber is positioned below the sedimentation chamber when the sample chamber is positioned in the cytocentrifuge device.

10. The sample chamber for use in a cytocentrifuge device according to claim 9, wherein the communication passage opening into the sedimentation chamber extends through the sedimentation chamber floor.

11. The sample chamber for use in a cytocentrifuge device according to claim 1, wherein the liquid removal chamber includes an absorbent material to absorb the sample liquid.

12. The sample chamber for use in a cytocentrifuge device according to claim 1, wherein the sedimentation floor is substantially horizontal when the sample chamber is positioned in the cytocentrifuge device.

13. The sample chamber for use in a cytocentrifuge device according to claim 1, wherein the passage from the sample receiving well into the sedimentation chamber introduces the sample from the sample receiving well into the sedimentation chamber near the top of the sedimentation chamber.

14. The sample chamber for use in a cytocentrifuge device according to claim 1, wherein the passage from the sample receiving well into the sedimentation chamber introduces the sample from the sample receiving well into the sedimentation chamber at the inner end of the sedimentation chamber.

15. The sample chamber for use in a cytocentrifuge device according to claim 1, wherein the passage from the sample receiving well into the sedimentation chamber includes a spillway from the sample receiving well into the inner end of the sedimentation chamber.

16. The sample chamber for use in a cytocentrifuge device according to claim 15, wherein the sample receiving well includes a bottom and a side that slopes upwardly from the bottom to the spillway.

17. The sample chamber for use in a cytocentrifuge device according to claim 16, wherein the spillway is positioned at the top of the inner end of the sedimentation chamber.

18. The sample chamber for use in a cytocentrifuge device according to claim 1, wherein the sample receiving well includes a top.

19. The sample chamber for use in a cytocentrifuge device according to claim 18, wherein the top of the sample well includes a pipette port for loading a sample into the sample receiving well.

20. The sample chamber for use in a cytocentrifuge device according to claim 1, wherein the sealing material is an absorbent material.

21. The sample chamber for use in a cytocentrifuge device according to claim 20, wherein the sealing material is compressed against the microscope slide to reduce its absorbancy during centrifugation.

22. The sample chamber for use in a cytocentrifuge device according to claim 21, wherein the sealing material is a closed cell plastic foam material.

23. The sample chamber for use in a cytocentrifuge device according to claim 1, wherein the sealing material includes a sealing material in combination with an absorbent material.

24. The sample chamber for use in a cytocentrifuge device according to claim 23, wherein the sealing material is compressed during centrifugation causing the material to be less absorbent than when centrifugation stops.

25. The sample chamber for use in a cytocentrifuge device according to claim 1, wherein the sample chamber includes means for removably mounting the sample chamber on a cytocentrifuge rotor.

26. The sample chamber for use in a cytocentrifuge device according to claim 25, wherein the means for removably mounting the sample chamber on a centrifuge rotor includes a clamping arm receiving compartment.

27. The sample chamber for use in a cytocentrifuge device according to claim 26, wherein the clamping arm biases the sample chamber against the microscope slide.

28. A sample chamber to be secured to a rotor in a cytocentrifuge device for receiving and distributing a sample containing sediment material to be deposited onto a microscope slide during centrifugation, the rotor having a center about which the rotor rotates during centrifugation, comprising:

a sample receiving well for receiving and holding the sample prior to centrifugation;

a sedimentation chamber to receive the sample from the sample well during centrifugation, said sedimentation chamber arranged in the sample chamber to be substantially horizontally oriented in a radial direction from the center of the rotor, wherein said sedimentation chamber comprises a floor, an outer open sedimentation end away from the center of the rotor and an inner end toward the center of the rotor when the sample chamber is positioned on the rotor, the open sedimentation end adapted to be positioned adjacent a microscope slide allowing the sample in the sedimentation chamber to collect in the sedimentation chamber under the influence of centrifugal force toward the open sedimentation end thereof to allow sediment material from the sample to contact the microscope slide during centrifugation and forming a vacant space at the inner end of the sedimentation chamber during such centrifugation;

a passage from the sample receiving well into the sedimentation chamber whereby sample will flow under centrifugal force from the sample receiving well into the sedimentation chamber during centrifugation;

a liquid removal chamber communicating with the sedimentation chamber at a location in the vacant space in the sedimentation chamber during centrifugation so as not to remove sample from the sedimentation chamber during centrifugation but to remove sample liquid from the sedimentation chamber when centrifugation stops and sample liquid flows into the vacant space;

a communication passage between the liquid removal chamber and the sedimentation chamber, opening into the sedimentation chamber adjacent the inner end and floor of the sedimentation chamber; and means for sealing provided around the open sedimentation end of the sedimentation chamber.

29. The sample chamber to be secured to a rotor in a cytocentrifuge device according to claim 28, wherein the sedimentation chamber further comprises an inner end wall and side walls, and wherein the communication passage opening into the sedimentation chamber extends through at least one of the inner end wall and the side walls.

30. The sample chamber to be secured to a rotor in a cytocentrifuge device according to claim 29, wherein there are two liquid removal chambers, each chamber being located on opposing sides of the sedimentation chamber, wherein the liquid removal chambers have removal chamber floors substantially aligned with the sedimentation chamber floor, wherein the liquid removal chambers extend upwardly from the removal chamber floors, and wherein the liquid removal chamber includes an absorbent material to absorb the sample and draw sample from the sedimentation chamber.

31. The sample chamber to be secured to a rotor in a cytocentrifuge device according to claim 28, wherein the liquid removal chamber is positioned below the sedimentation chamber when the sample chamber is positioned in the cytocentrifuge device.

32. A method for removing sample liquid remaining in a sample chamber for use in a cytocentrifuge device for receiving and distributing a sample containing sediment material to be deposited onto a microscope slide during cytocentrifugation, comprising steps of:

providing a sample chamber comprising:

a sample receiving well for receiving and holding the sample prior to centrifugation, a sedimentation chamber comprising a floor, an outer open sedimentation end and an inner end, the open sedimentation end adapted to be positioned adjacent a microscope slide so that the sample will collect in the sedimentation chamber toward the open sedimentation end allowing sediment material from the sample in the sedimentation chamber to contact and adhere to the microscope slide during centrifugation and forming a vacant space at the inner end of the sedimentation chamber during centrifugation, a passage from the sample receiving well into the sedimentation chamber whereby sample will flow under centrifugal force from the sample receiving well into the sedimentation chamber during centrifugation, at least one liquid removal chamber in communication with the vacant space in the sedimentation chamber during centrifugation to remove sample liquid from the sedimentation chamber when centrifugation stops and sample liquid flows into the vacant space;

a communication passage between the liquid removal chamber and the sedimentation chamber, opening into the sedimentation chamber adjacent the inner end and floor of the sedimentation chamber; and a sealing material surrounding the open end of the sedimentation chamber for sealing against the microscope slide when the sample chamber is positioned in a cytocentrifuge device against a microscope slide, sizing the sedimentation chamber to have a volume larger than the sample volume of the sample receiving well so that the sample will collect in the sedimentation chamber toward the open sedimentation end of the sedimentation chamber during centrifugation and such that the sample liquid will flow back into the vacant space in the sedimentation chamber when centrifugation stops; and positioning the communication passage such that said communication passage opens into the vacant space in the sedimentation chamber during centrifugation so as not to remove sample liquid from the sedimentation chamber during centrifugation but to remove sample liquid from the sedimentation chamber when centrifugation stops and sample liquid flows into the vacant space and through the communication passage into the at least one liquid removal chamber.

33. The method for removing sample liquid remaining in a sample chamber for use in a cytocentrifuge device according to claim 32, wherein the sedimentation chamber further comprises an inner end wall and side walls, and wherein the step of positioning where the communication passage opens into the sedimentation chamber extends the communication passage through at least one of the inner end wall and the side walls.

34. The method for removing sample liquid remaining in a sample chamber for use in a cytocentrifuge device according to claim 33, wherein the step of providing at least one liquid removal chamber includes the step of providing two liquid removal chambers, each liquid removal chamber being located on opposing sides of the sedimentation chamber and having liquid removal chamber floors substantially aligned with the sedimentation chamber floor, and wherein the liquid removal chambers extend upwardly from the liquid removal chamber floors, and the method further comprises step of providing an absorbent material in the at least one liquid removal chamber to absorb the sample liquid and draw sample liquid from the sedimentation chamber.

35. The method for removing sample liquid remaining in a sample chamber for use in a cytocentrifuge device according to claim 32, wherein the step of providing at least one liquid removal chamber includes the step of providing a liquid removal chamber positioned below the sedimentation chamber when the sample chamber is positioned in the cytocentrifuge device, and wherein the step of positioning where the communication passage opens into the sedimentation chamber extends the communication passage through the sedimentation chamber floor.

36. The method for removing liquid sample remaining in a sample chamber for use in a cytocentrifuge device according to claim 32, wherein the step of providing the sample chamber with the sealing material surrounding the open end of the sedimentation chamber includes providing an absorbent sealing material around the open end of the sedimentation chamber which absorbs sample liquid from the microscope slide at the open end of the sedimentation chamber when centrifugation stops.

* * * * *